(12) United States Patent
Schermerhorn et al.

(10) Patent No.: US 7,303,392 B1
(45) Date of Patent: Dec. 4, 2007

(54) APPARATUS, METHOD, AND KIT FOR FABRICATING DENTAL CLASPS

(76) Inventors: Kris Schermerhorn, 18913 White Oak Dr., Triangle, VA (US) 22172; Richard E. Schermerhorn, 18335 Sharon Rd., Triangle, VA (US) 22172; V. Kim Kutsch, 1155 Twin Hills Dr., Jefferson, OR (US) 97352; Robert J. Bowers, 3170 26th Ave., SE., Albany, OR (US) 97322; Jesse L. Droesch, 3093 27th Ave., SE., Albany, OR (US) 97322

(*) Notice: Subject to any disclaimer, the term of this patent is extended or adjusted under 35 U.S.C. 154(b) by 99 days.

(21) Appl. No.: 11/125,255

(22) Filed: May 9, 2005

Related U.S. Application Data

(60) Provisional application No. 60/569,700, filed on May 10, 2004.

(51) Int. Cl.
*A61C 9/00* (2006.01)
*A61C 5/04* (2006.01)
*A61C 19/00* (2006.01)

(52) U.S. Cl. .............................. 433/36; 433/90; 433/32

(58) Field of Classification Search .................. 433/34, 433/35, 36, 90; 89/1.12; D19/70; 219/240, 219/492; 222/146.5, 333, 326–327, 390
See application file for complete search history.

(56) References Cited

U.S. PATENT DOCUMENTS

| 2,437,264 | A | * | 3/1948 | Manning | ..................... 156/167 |
| 5,846,082 | A | * | 12/1998 | Thornton | ..................... 433/215 |
| 6,855,278 | B2 | | 2/2005 | Lichkus et al. | ............... 264/18 |

OTHER PUBLICATIONS

Pending U.S. Appl. No. 10/166,429, filed Jun. 10, 2002, Kutsch, VK et al., Materials and Methods for Producing Dental Prostheses.
www.cdmonline.biz/labs/training/HSGtraining/HotShot AcetalClaspGunManual.

* cited by examiner

*Primary Examiner*—Cris Rodriguez
*Assistant Examiner*—Candice C. Stokes
(74) *Attorney, Agent, or Firm*—Lori M. Friedman

(57) ABSTRACT

The invention disclosed herein relates to an efficient and inexpensive way to form dental clasps and fixed single unit temporary prostheses from molten thermoplastic resin. The apparatus and method allow a dental laboratory to make non-metallic clasps using an inexpensive handheld thermoplastic injection unit/gun that injects molten resin into a model of the clasp made from wax. A silicone putty matrix allows the resin to flow into a vacated wax model of the clasp. The time and money needed for this is much less than is needed to create such clasps using hot press equipment.

20 Claims, 5 Drawing Sheets

APPARATUS, METHOD, AND KIT FOR FABRICATING DENTAL CLASPS

RELATED PATENT APPLICATIONS

This is a utility patent application based on a U.S. Provisional patent application Ser. No. 60/569,700 filed May 10, 2004

FIELD OF THE INVENTION

The present invention relates to an apparatus, method and kit for fabricating dental clasps and fixed single unit temporary crowns from thermoplastic resins. The dental clasps and single unit temporary crowns of this invention will be non-metallic and their color will be clear or close to that of the gingiva and/or tooth.

BACKGROUND OF THE INVENTION

For many years dental prostheses have been made for patients who have lost any number of their natural teeth. Prostheses of interest in the present invention are partial dentures, fixed temporary single unit temporary crowns as well as orthodontic appliances. Of prime interest to a patient needing artificial teeth is their appearance. The patient expects his or her dentist to be able to restore missing teeth with prostheses that both function comfortably for biting and chewing food and look esthetically pleasing. Dentists requiring such prostheses often employ the services of a dental laboratory, which is outfitted with the equipment and personnel required to build such prostheses, including computer aided design and manufacture equipment (CAD/CAM).

Since the patient's dental restoration will be visible to others, most dentists and patients are eager to have prostheses that look natural. If the prosthesis is for only one or two teeth and the patient has mostly natural teeth, a good match between the prosthesis and the natural dentition is very highly desirable.

Not only is the color match to the teeth and gums critically important, most patients do not want a metallic clasp attaching the prosthesis to their natural teeth to be visible. Even if the teeth of the prosthesis are well-matched, a metal clasp attaching it to the natural teeth indicates that they are false.

Dental prostheses are divided into two categories, fixed and removable. Fixed prostheses are tooth and/or implant supported prostheses that are bonded or cemented into place and are not routinely removed by the patient. The removable prostheses of concern in this patent application include partial dentures, bite or occlusal appliances, orthodontic appliances, snoring and sleep apnea appliances. Of prime interest in this patent application are temporary fixed single unit crowns and removable partial denture clasps.

Partial dentures are tooth, tissue and/or implant supported and is removable by the patient for routine cleaning and home care. The occlusal, orthodontic, snoring, mouth guard and sleep apnea appliances may be supported by tooth, implant, tissue or a combination thereof. The fixed single unit temporary crowns are cemented or bonded to place. They will be fixed to ether a prepared natural tooth or an implant abutment. They will remain in the mouth from a time period ranging from a few weeks to several months while the permanent crown is being made or while the patient's mouth is healing from surgery.

Temporary and provisional prostheses are sometimes made by the dentist but are generally fabricated by a dental laboratory. Partial dentures can have a metal substructure or be all acrylic and support a clasp. The non-metallic dental clasps that are the subject of this invention are also applicable and of use in orthodontia. Even though the detailed description describes clasps for partial dentures, it is understood that the description applies to orthodontic and other appliances as well.

In the past, dentists have had a variety of options when working with dental laboratories making prostheses for their patients. Esthetics, as well as cost, is of interest to all parties concerned. Until the present invention, dental lab customers often would choose between esthetics and cost.

An option that exists for fabricating dental clasps is a pre-formed clasp made of non-metallic material. These pre-formed clasps are bought pre-made from a company and then fitted to a particular prosthesis by hand. To get a pre-formed clasp in place, a channel is cut into the partial denture, and then the clasp is heated until it is pliable. At that time, the softened clasp is pushed into place on the partial denture by the dental technician.

In the past, as seen in U.S. Pat. No. 6,855,278 Lichkus et al discuss a process of making a dental prosthesis with a clear aesthetic clasp. The clasp of the '278 invention are not made of an acetal resin that is color-coordinated to the patient's tooth and gingiva as are the clasps of the instant invention.

The method claimed in '278 does not use the delivery method of this invention. Unlike the present invention, it requires the use of hot-press dental equipment. This adds to the cost, time needed to make the clasps, and the amount of material used to make the clasps.

Most dental laboratories do not use thermoplastic resins to fabricate clasps for dental prostheses. This is because until the present invention expensive hot-press equipment is needed, which is unavailable to most dental laboratories. The present invention uses a hand-held thermoplastic injection gun to make clasps out of thermoplastic resin without the need for expensive hot press equipment.

Acetal resin, the preferred material of use of this invention, is a highly crystalline thermoplastic, non-amorphous material. The material is an encapsulated polyoxymethylene copolymer of non-volatile cylindrical pellets. The characteristics of highly crystalline polymer include low to almost no water absorption and therefore no problems with bacteria and stain build up on acetal resin. The material will remain color stable for the life of the acetal resin. The low moisture absorption and chemical resistance of acetal resin allows it to be very resistant to deterioration over time. A preferred acetal resin of the present invention is sold as "Aesthetic Perfection" and is made and distributed by CDM, Inc. Albany, Oreg.

Besides avoiding the additional expense that has been mentioned, the current invention also takes significantly less time to form thermoplastic clasps than the hot-press equipment would take. Another positive feature of the dental clasp of the present invention is that less raw material used and less wasted, in making the clasps with the hand-held thermoplastic injection gun of this invention.

DEFINITIONS USED IN THIS INVENTION

The following definitions are provided solely for the benefit of the reader, and should not be construed to limit the terms to any specific examples provided. They should also not be construed to be narrower than those accepted by persons of ordinary skill in the art.

In this invention, a 'clasp' will mean the portion of a removable partial prosthesis that rests on and encompasses the abutment teeth so that so as to retain the partial denture and stabilize both the denture and the abutment teeth In this invention, 'sprue' will mean the wax used to form the aperture through which a thermoplastic enters a mold to make a casting; it also may refer to the material that later fills a sprue hole (or holes)

In this invention, 'thermoplastic resins' are the material used in fabrication in the equipment of this invention that are selected from the group consisting of homopolymers and copolymers acetal, resins and nylon, as well as compatible mixtures of these materials.

In this invention, 'dimple' will mean to indent the silicone putty matrix with an outline of itself that will become a sprue for molten thermoplastic resin to flow and form the dental clasp.

In this invention, 'matrix' will mean the medium in which molds of desired objects are made.

In this invention, 'invest' will mean to surround, envelop, or embed in a matrix.

In this invention, 'Shore hardness' will be used as a method of rating the hardness and/or flexibility of the putty used in this invention.

In this invention, 'tissue' will mean the gingiva (gums) in the mouth.

In this invention, 'thermoplastic resin in colors that blends with the teeth and gingiva of a patient' will include those resins colored to blend with a person's dentition as well as clear or colorless materials such as nylon. In all cases, the clasps and prostheses of this invention are non-metallic and not visible or noticeable to onlookers.

SUMMARY OF THE INVENTION

The present invention includes an apparatus that makes dental clasps out of thermoplastic resin without the use of expensive hot-press equipment. The apparatus disclosed herein is a hand-held thermoplastic injection gun.

The hand-held thermoplastic injection gun could be constructed from scratch or be constructed by modifying an existing glue gun with the proper specifications. The injection piston of the gun could be mechanically driven as in the current invention, or could be driven pneumatically or hydraulically.

The gun has a barrel and a trigger, the barrel having two ends and a longitudinal internal heating element located therebetween, an opening at the first end of the barrel which accepts a funnel into which is poured solid pellets of thermoplastic resin material and whose second end terminates in a nozzle which delivers molten thermoplastic resin through a tip for use in a silicone putty matrix on to plaster dental mold to make the clasp.

The gun also includes a removable ratcheting rod with notched pre-cut grooves which moves with piston-like movement when the gun's trigger is squeezed. The grooves of the ratcheting rod match the teeth on the mechanical linkage. The mechanical linkages advance the ratcheting rod in the barrel when the trigger is manually squeezed. The ratcheting rod is advanced about ten mm each time the gun is squeezed.

The gun has a hollow metal tip that delivers molten thermoplastic resin to a silicone putty matrix. The matrix surrounds the plaster dental mold which has contained inside a wax replicate of the desired dental clasp. A separate, solid metal tip that exactly matches the size and dimensions of the hollow metal tip of the nozzle of the gun is used to dimple the silicone putty matrix with an outline of itself that will become a sprue for molten thermoplastic resin to flow and form the dental clasp.

The indentation made by the solid metal tip spans a distance of about 4-5 mm. The indented putty matrix surrounds the plaster dental mold which has contained inside a wax replicate of the desired dental clasp. The two identical tips ensure correct fit and tight sealing of the mold that produces a thermoplastic resin dental clasp.

The following figures and detailed description of preferred embodiments will further elucidate the apparatus and method of use of the invention. A kit that enables the use of the various aspects of the invention is also provided.

DETAILED DESCRIPTION OF PREFERRED EMBODIMENTS

Figure 1:
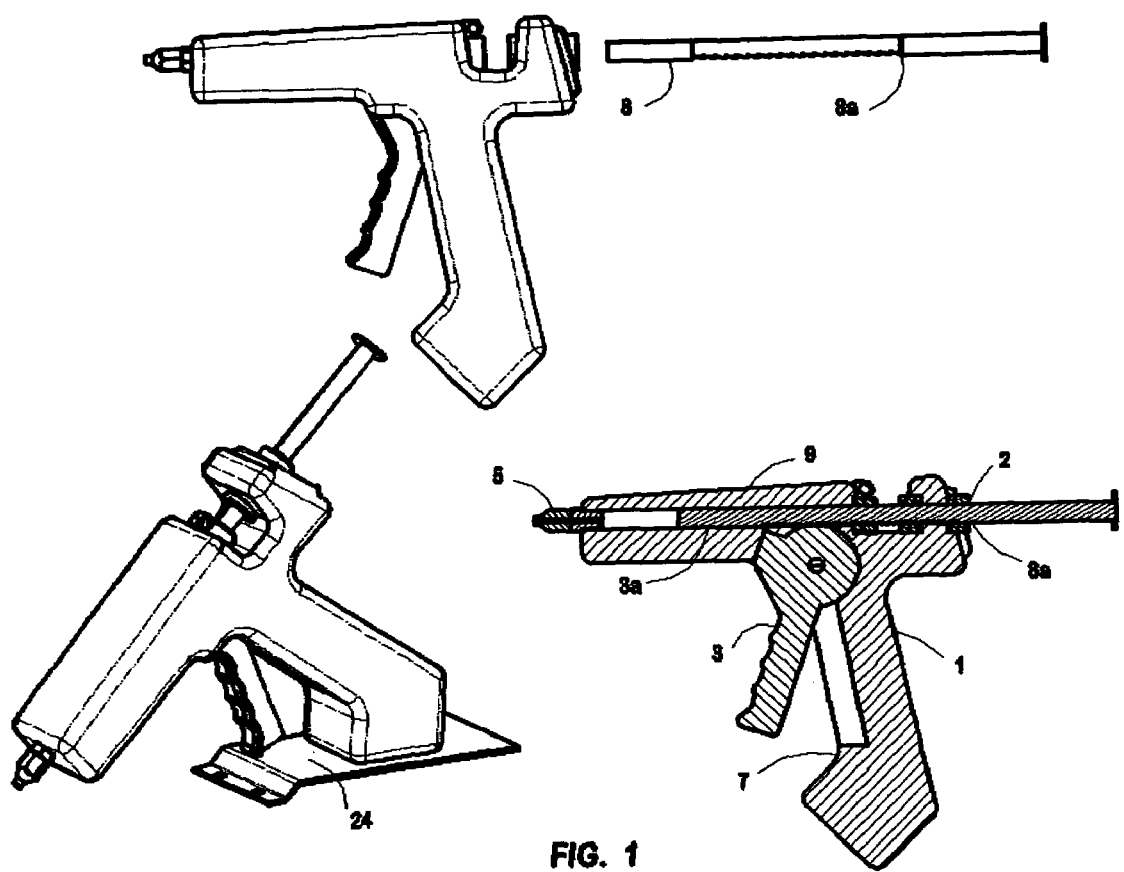
FIG. 1 depicts the modified glue gun that is the apparatus of this invention.
Figure 2:
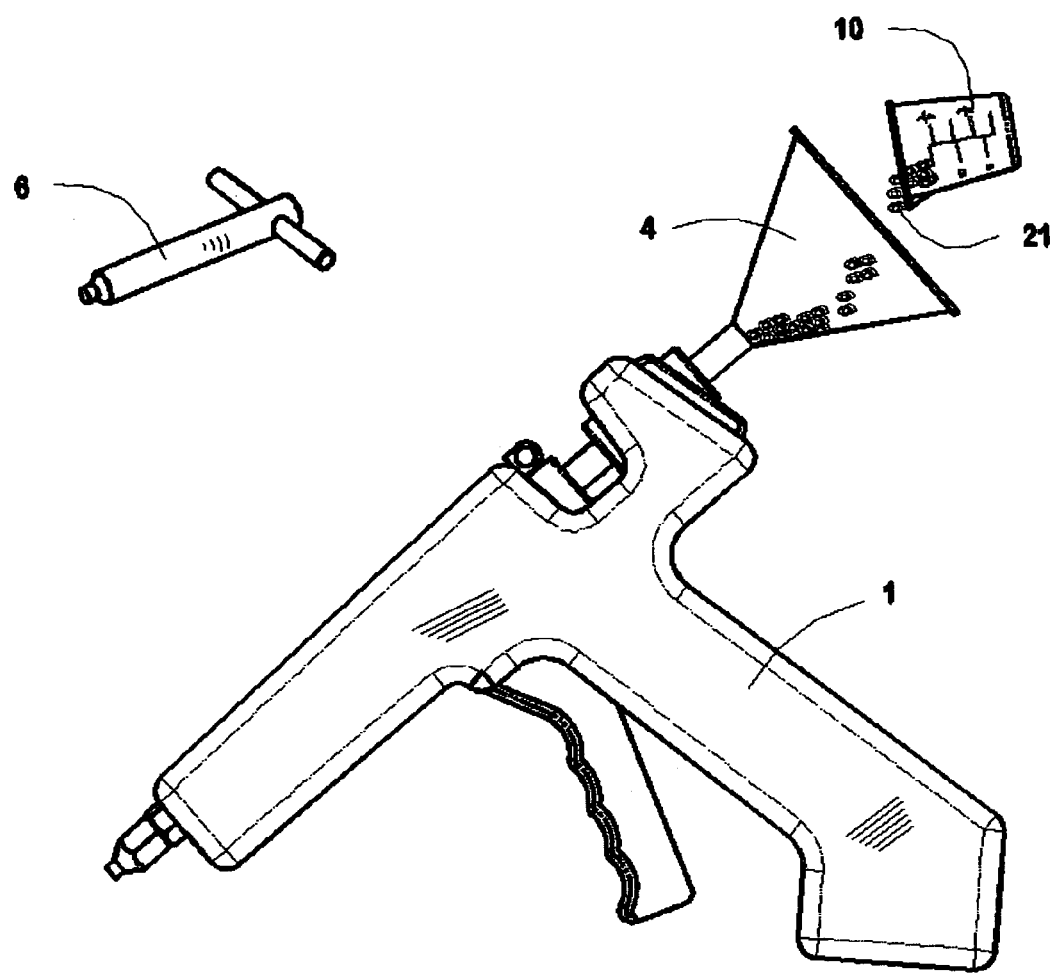
FIG. 2 shows the gun of FIG. 1 with the details of filling its barrel with solid pellets of thermoplastic resin and also shows a solid metal replicate of the gun's hollow tip.
Figure 3:
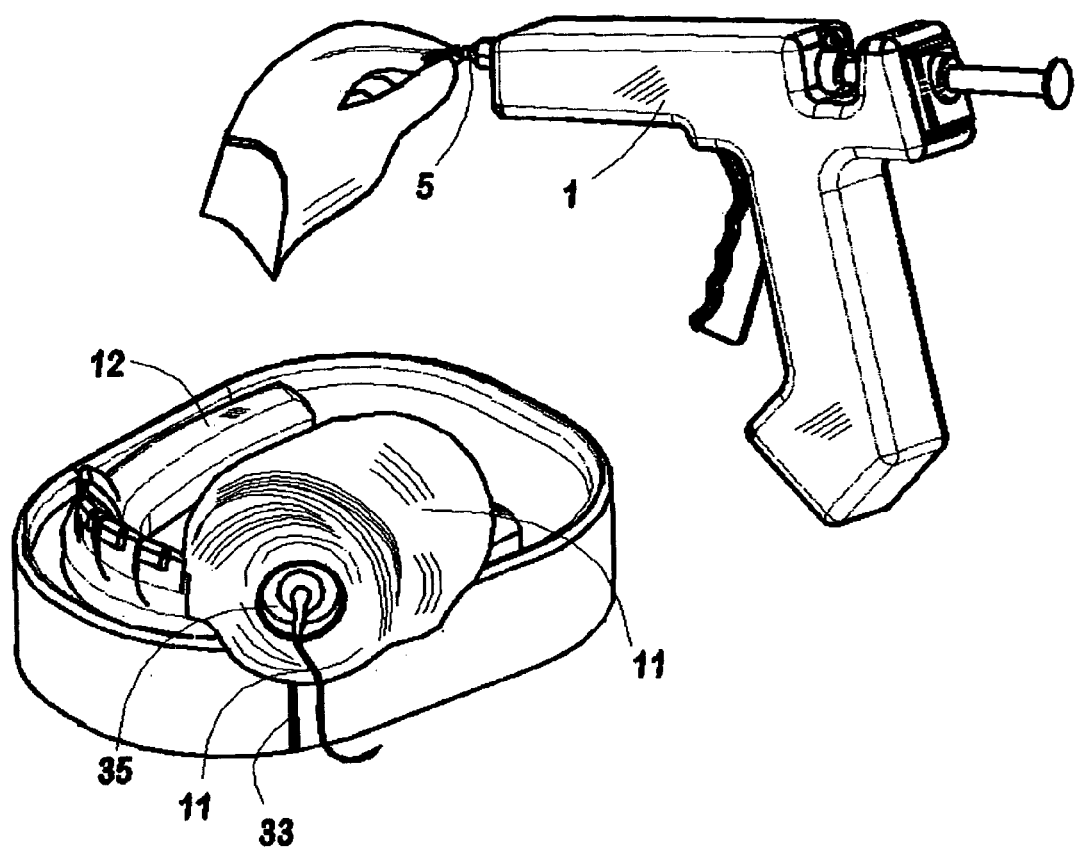
FIGS. 3 and 4 show a series of views of a plaster dental mold, the putty which covers it, and the clasp being formed by the apparatus of this invention.
Figure 4A:
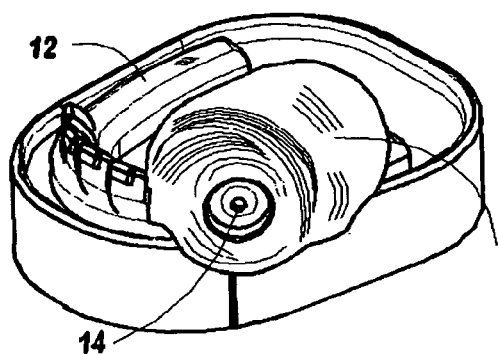
Figure 4B:
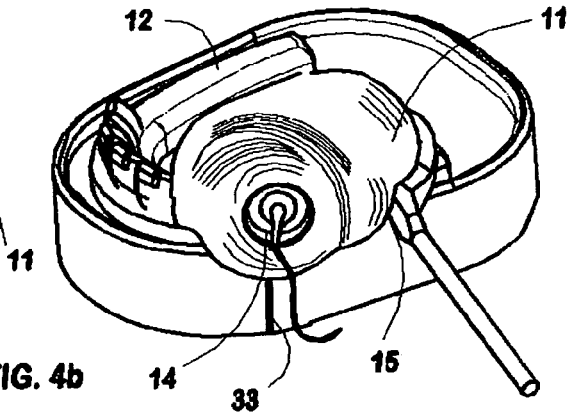
Figure 4C:
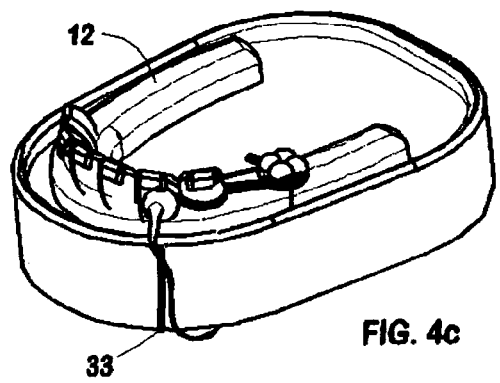
Figure 4D:
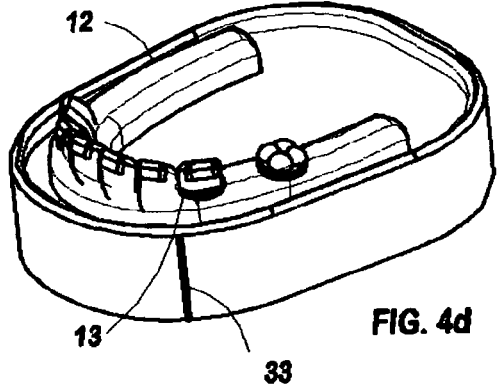

With reference to FIGS. 1, 2, and 3 the first step that is taken to make a clasp 13 of thermoplastic resin is to make a wax model of the clasp. First a plaster dental model 12 of the teeth that will outline a clasp 13 that will hold a partial denture or similar removable dental prosthesis in places made. It is made from 12 gauge sprue rope wax by a routine procedure well known and often used by dental laboratories. The wax clasp 13 should be as close to the finished clasp as possible and should be 2 mm in diameter.

While the wax model of the clasp 13 is being made and is hardening, a putty matrix 11 is compounded from two parts 20A and 20B, 20A and 20B are a two-part silicone putty matrix wherein one is the silicone polymer and the other is a curative. The mixed putty will have a Shore hardness of at least 90. Silicone putty is routinely used for the production of dentures and dental prostheses. The putty is made of two parts; an organopolysiloxane mixture (part A), and a crosslinker (part B).

An example of a preferred silicone putty in the present invention is made by the Silpak Company of Pomona, Calif. Silpak's Silputty (Silputty, Silputty 40, Silputty LV) Series are platinum based, one-one mix, quick curing silicone room-temperature vulcanizates (RTVs).

The next steps of the process are shown in FIG. 4. Before combining the putty ingredients, the tip of the clasp 13 is marked with a pen mark 33 on the lower facial and lingual areas. After the putty 11 is mixed, it will be applied on the model 12 to cover the facial and lingual areas surrounding the clasp 13. Before the putty 11 hardens, it is dimpled with the solid metal tip 6 that is an exact replicate of the hollow nozzle tip 5 of the gun 1 of this invention. The dimple 35 is placed in line with the pen mark 33 on the model to ensure that the dimpled area is close the tip of the waxed clasp 13. This is done before the gun 1 is loaded with thermoplastic resin pellets 21. The solid metal tip 6 can be removed after its image is dimpled in the putty 11. After the putty 11 is dimpled, removal of the solid metal tip 6 is necessary.

The next step of this process is to remove the hardened putty matrix 11. The putty matrix 11 is semi-flexible so that removal is not difficult. The hole 14 is drilled by holding the putty matrix 11 and drilling one hole with a round burr (not shown) that is 1.5. to 2.5 mm in diameter straight into the hardened silicone putty matrix 11. This is to allow the molten thermoplastic resin 21 to flow into the now empty model 12 to become the clasp 13. If the drilled hole 14 does not connect to the tip of the wax model of the clasp 13, the burr is then used to drill a channel into the putty matrix 11 to extend to the tip of the clasp 13.

After the hole 14 drilled, air is blown into the putty matrix 11 to clear it of dust and other debris from the drilling. After the hole 14 is drilled, the model is immersed into boiling water to remove the wax clasp 13. Then the putty matrix 11 is placed back on the model and placed back in the boiling water to preheat the model to accept the warm thermoplastic resin 21.

The next series of steps now concern using the gun 1 of this invention to melt an amount of thermoplastic resin pellets 21 that will become a thermoplastic clasp 13. At this time, as shown in FIG. 2, an amount of thermoplastic resin pellets 21 is measured in a cup 10 to the 10 ml line and poured into a funnel 4. The quantity of material used weighs about 8 grams. The thermoplastic resins 21 usable in the invention are homo-polymer and co-polymer acetal, nylon co-polymers and compatible mixtures thereof.

Prior to inserting the funnel 4 into the funnel-accepting end of the gun's barrel 2, the ratcheting rod 8 is removed from the gun. The ratcheting rod 8 of this invention is 10 inches long; the size of the gun 1 itself, the grip 7, and all the other parts itemized and described herein are sized accordingly. After the thermoplastic pellets 21 are poured into the gun's barrel 2, the gun is turned on. A timer (not shown) is set for 14 minutes. While the time is passing, the putty matrix 11 is put back on the plaster model 12. Both are then put in clean boiling water for immersion and preheating.

When the timer sounds, the materials are removed from the boiling water and left undisturbed for a period of time of at least 30 seconds and no longer than one minute. Now the ratcheting rod 8 is placed, with its teeth face down, into the gun 1, which has been heating the pellets of thermoplastic resin 21. An operator manually squeezes the gun's trigger 3 until a sufficient quantity of molten thermoplastic resin 21 is ejected to expel resin with bubbles or porosity. The material should be injected until the ring 8a on the back of the ratcheting rod 8 reaches the back of the gun 1. About eight trigger pulls are required to eject about 80 mm of molten thermoplastic resin to form up to two clasps; the amount being enough to form said clasps.

The tip 5 of the gun 1 is then ready to eject molten thermoplastic resin 21 to the empty area that was the wax model of the clasp 13. The tip of the gun 5 is placed in the pre-formed hardened putty 11. By compressing the trigger of the gun 1 and holding for five seconds the molten thermoplastic resin 21 is ejected out of the gun's nozzle 5 with one or two pulls of the trigger 3. The molten thermoplastic resin 21 flows into the outline that the solid metal nozzle tip 6 made in the silicone putty 11 to become the clasp 13. The process is finished by cooling, cutting off the silicone putty matrix, and contouring the finished thermoplastic resin clasp 13 as desired.

The process of making a clasp 13 for dental prostheses as described herein represents a significant savings in both time and money to dental labs, dentists and patients. The method of this invention lessens the time needed for forming a dental clasp to less than one hour.

Figure 5:
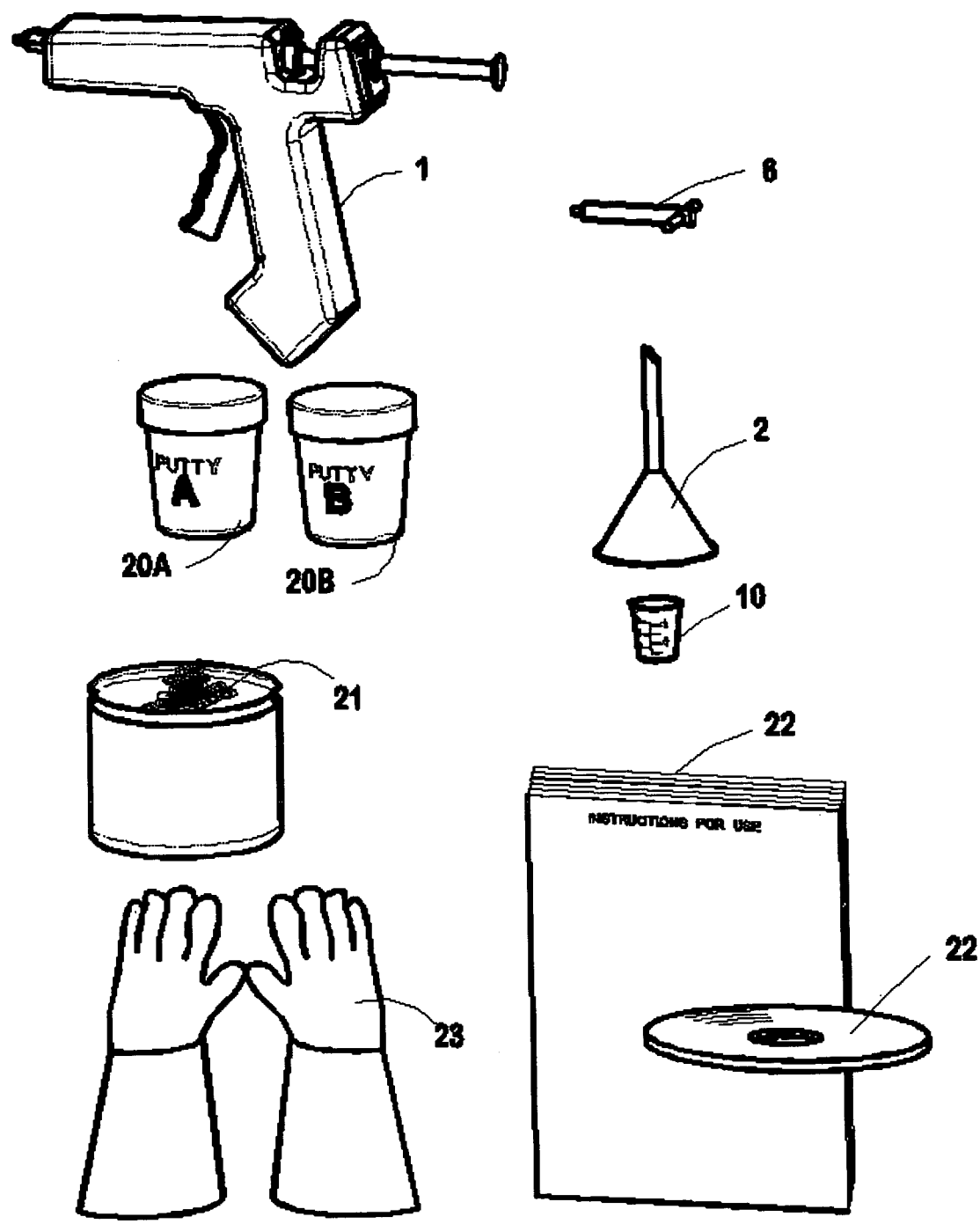
FIG. 5 illustrates the components of the kit of this invention.

FIG. 4 shows four different views, labeled 4a, 4b, 4c, and 4d. FIG. 4 shows the progression of the present invention: FIG. 4a, in the upper left of FIG. 4, shows a mold awaiting injection. FIG. 4b, in the upper right of FIG. 4 depicts the breaking of the mold after the putty has hardened. FIG. 4c, in the lower left of FIG. 4 shows the remnants of the molding process (runners, sprue, and the like) prior to trimming, and FIG. 4d, the lower right of FIG. 4 is a finished clasp Also included in this invention is a kit, as shown in FIG. 5. The kit supplies materials needed for the methods of making dental clasps 13 from molten thermoplastic resin 21 described herein. The kit includes a hand-held thermoplastic injection gun 1 with a barrel 3a and a trigger 3, said barrel having two ends and a longitudinal internal heating element (not shown) located therebetween, an opening at the first end of the barrel 2 which accepts a funnel 4 into which is poured solid pellets of thermoplastic resin 21 and whose second end terminates in a nozzle 5 with a tip that delivers said molten thermoplastic resin 21 through the tip for use in a silicone putty matrix 11 on to plaster dental model 12 to make a clasp 13. The gun 1 also includes a removable ratcheting rod 8 with notched pre-cut grooves which move with piston-like movement when the gun's trigger 3 is manually squeezed, the grooves of said ratcheting rod 8 which match the grooves in the gun's mechanical linkage The kit also includes an amount of two-part silicone putty 20A and 20B, provided in sealed jars labeled part A and part B, which are combined in equal amounts, kneaded with the fingers, and placed over the dental plaster model 12 with a wax model of the desired clasp 13, a funnel 4 that fits into the first end 2 of the gun for delivering thermoplastic resin pellets 21 into the gun for melting, two bottles of thermoplastic resin or smaller amounts measured for smaller, individual loads of about 8 grams of resin pellets 21, a solid metal tip 6 that is a solid exact replicate of the hollow nozzle tip 5 of the gun that dimples a silicone putty matrix 11.

Also included in the kit are a pair of nylon gloves 23 and a set of instructions for use 22. The instructions are provided in written form as well as in the electronic form of a DVD/video. The instructions are also available on the web site of Cosmetic Dental Materials, who supplies the kits and various materials of this invention, including the 'HotShot' acetyl clasp gun. The address for CDM is http://cdmonline.biz.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

What is claimed is:

1. An apparatus for forming a dental clasp from thermoplastic resins including a gun with a barrel and a trigger, the barrel having two ends and a longitudinal internal heating element located therebetween for heating solid thermoplastic resin to a molten state, an opening at the first end of the barrel which accepts a funnel into which is poured solid pellets of thermoplastic resin material and whose second end terminates in a nozzle which delivers molten thermoplastic resin through a tip for use in a silicone putty matrix on to plaster dental mold to make the clasp, the gun also includes a) a removable ratcheting rod with notched pre-cut grooves which moves with piston movement when the gun's trigger is manually squeezed, the grooves of the ratcheting rod that matches grooves in the gun's mechanical linkage thus advancing the rod to expel molten thermoplastic resin when the trigger is squeezed, b) a hollow metal tip that delivers the molten thermoplastic resin to the silicone putty matrix that surrounds a wax replicate of the clasp on the plaster dental mold which has contained inside the wax replicate of the dental clasp; and a separate, solid metal tip that exactly matches the size and dimensions of the hollow metal tip of the nozzle of the gun that is used to indent the silicone putty matrix with an outline of itself that will become a place to engage the tip of the gun so the gun will have a good seal to the putty matrix when squeezed to eject molten resin to form the clasp.

2. The apparatus of claim 1 wherein the fabricated thermoplastic resin dental clasps are made of thermoplastic resin in colors that blend with the teeth and gingiva of a patient.

3. The apparatus of claim 1 wherein the gun has mechanical linkages which advance the ratcheting rod in the barrel when the trigger is manually squeezed.

4. The apparatus of claim 3 wherein both the ratcheting rod and the mechanical linkage of the gun are both notched with identical patterns such that squeezing the gun's trigger advances the ratcheting rod about 10 mm.

5. The apparatus of claim 4 wherein about eight trigger pulls are required to eject about 80 mm of molten thermoplastic resin to form up to two clasps; the amount being enough to form said clasps.

6. The apparatus of claim 1 wherein the putty matrix comprises a two-part silicone putty matrix which, after mixing and room-temperature curing, has a Shore hardness of at least 90.

7. The apparatus of claim 1 wherein the hollow metal tip and the exactly matching solid metal tip ensure correct fit and tight sealing of the mold that produces a clasp made of thermoplastic resins that are selected from the group consisting of homopolymers and copolymers acetal, resins and nylon, as well as compatible mixtures of these materials.

8. The apparatus of claim 1 wherein the wax replicate dental clasp becomes a clasp made of thermoplastic resin.

9. A method for forming a dental clasp in shades that blend with a patient's dentition and gingiva out of thermoplastic resins selected from the group consisting of homopolymers and copolymers acetal resins and nylon, as well as compatible mixtures of these materials, requiring first creating a wax model of the clasp in a mold and then making the clasp from said thermoplastic resin comprising the steps of a) creating a plaster dental model and a clasp replicated in wax;

b) marking each tip of the wax clasp replicate on both the lower facial and lingual areas with a pen to signify where the wax model of each clasp tip is in the model; and then c) mixing a two-part silicone putty matrix;

d) putting the silicone putty matrix on the model to cover the area around the waxed clasp.

e) placing a solid metal nozzle tip into the putty in line with the pen marks on the facial and lingual, said solid metal nozzle being a solid replicate of a hollow metal nozzle tip of the gun with an internal heating element, which will melt a desired amount and color of thermoplastic resin material that will become the clasp;

f) waiting at least fourteen minutes for the measured thermoplastic resin loaded in the gun to melt;

g) squeezing the trigger of the gun forcing molten thermoplastic resin to eject out of the gun's nozzle;

h) injecting molten thermoplastic resin and holding for five seconds by squeezing the trigger, allowing the molten thermoplastic resin to flow into the outline that the solid metal nozzle tip has made in the silicone putty;

i) drilling one hole into the hardened silicone putty matrix to allow the molten thermoplastic resin to flow into the now empty model to become the clasp;

j) immersing the model into boiling water to remove the wax clasp and preheat the model to accept the warm thermoplastic resin;

k) finishing the process by cooling, cutting off the silicone putty matrix, and contouring the finished thermoplastic resin clasp as desired.

10. The method of claim 9 wherein the silicone putty matrix has a Shore hardness of at least 90.

11. The method of claim 9 wherein the thermoplastic resin clasp is about from 1.5 to 2.5 mm in diameter.

12. The method of claim 9 wherein the production of a dental clasp is done by a dental professional for prostheses selected from the group consisting of partial dentures, fixed temporary single unit temporary crowns, and orthodontic appliances.

13. The method of claim 9 wherein a significant cost savings is realized by patients, dentists and dental laboratories by its use.

14. The method of claim 9 wherein the time needed for forming a dental clasp is less than one hour.

15. A kit with materials for the fabrication of a dental clasp out of thermoplastic resins selected from the group consisting of homopolymers and copolymers acetal, resins and nylon, as well as compatible mixtures of these materials in colors that blend with the dentition and gingival of a patient comprising a) a handheld thermoplastic injection gun with a barrel and a trigger, said barrel having two ends and a longitudinal internal heating element located therebetween to heat and melt said thermoplastic resin, an opening at the first end of the barrel which accepts a funnel into which is poured solid pellets of said thermoplastic resin and whose second end terminates in a nozzle which delivers molten thermoplastic resin through a tip for use in a silicone putty matrix on to plaster dental mold to make the clasp, said gun also includes a removable ratcheting rod with notched pre-cut grooves which moves with piston-like movement when the gun's trigger is squeezed, the grooves of said ratcheting rod that match the grooves in the gun's mechanical linkage;

b) an amount of two-part silicone putty, provided in sealed jars labeled part A and part B, which are combined in equal amounts, kneaded with the fingers, and placed over a marked dental plaster model with a wax model of the desired clasp;

c) a funnel that fits into one end of the gun for delivering thermoplastic resin pellets into the gun for melting;
d) two bottles of thermoplastic resin or single 8 gram loads of thermoplastic resin;
e) a solid metal tip that is a solid replicate of the nozzle of the gun that indents silicon putty matrix a distance of about 4-5 mm, said putty matrix is indented and surrounds the plaster dental mold which has contained inside a wax replicate of the desired dental clasp;
f) a pair of synthetic rubber gloves;
g) a set of instructions for use.

16. The kit of claim 15 wherein the silicone putty matrix has a Shore hardness of at least 90.

17. The kit of claim 15 wherein the thermoplastic resin clasp is about 1.5-2.5 mm in diameter.

18. The kit of claim 15 wherein the production of a dental clasp by a dental laboratory for a prosthesis selected from the group consisting of partial dentures, fixed temporary single unit crowns, and orthodontic appliances.

19. The kit of claim 13 wherein a significant cost savings is realized by patients, dentists, and dental laboratories by its use.

20. The kit of claim 13 wherein the time needed for forming a dental clasp is less than one hour.

* * * * *